(12) United States Patent
Goldmann et al.

(10) Patent No.: US 8,728,151 B2
(45) Date of Patent: May 20, 2014

(54) WOVEN TEXTILE VASCULAR PROSTHESIS

(75) Inventors: Helmut Goldmann, Tuttlingen (DE);
Christof Merckle, Mannheim (DE)

(73) Assignee: Aesculap AG (DE)

( * ) Notice: Subject to any disclaimer, the term of this patent is extended or adjusted under 35 U.S.C. 154(b) by 870 days.

(21) Appl. No.: 12/334,581

(22) Filed: Dec. 15, 2008

(65) Prior Publication Data

US 2009/0171450 A1    Jul. 2, 2009

(30) Foreign Application Priority Data

Dec. 17, 2007 (DE) .......................... 10 2007 063 265

(51) Int. Cl.
*A61F 2/06* (2013.01)

(52) U.S. Cl.
USPC .......................... 623/1.51; 623/1.35; 623/1.52

(58) Field of Classification Search
USPC ................................ 623/1.51–1.54; 428/35.1
See application file for complete search history.

(56) References Cited

U.S. PATENT DOCUMENTS

| | | | |
|---|---|---|---|
| 2,924,250 A | | 2/1960 | Sidebotham |
| 3,095,017 A | | 6/1963 | Bleiler et al. |
| 4,517,687 A | * | 5/1985 | Liebig et al. ................. 623/1.52 |
| 4,816,028 A | * | 3/1989 | Kapadia et al. .............. 623/1.52 |
| 5,127,919 A | * | 7/1992 | Ibrahim et al. ............... 623/1.51 |
| 5,156,619 A | | 10/1992 | Ehrenfeld |
| 6,136,022 A | | 10/2000 | Nuñez et al. |
| 6,273,912 B1 | | 8/2001 | Scholz et al. |
| 6,589,278 B1 | | 7/2003 | Harris et al. |
| 6,814,754 B2 | * | 11/2004 | Greenhalgh ................. 623/1.51 |
| 2002/0042644 A1 | * | 4/2002 | Greenhalgh ................. 623/1.13 |
| 2002/0058992 A1 | * | 5/2002 | Greenhalgh ................. 623/1.35 |
| 2005/0240261 A1 | | 10/2005 | Rakos et al. |
| 2007/0005128 A1 | | 1/2007 | Scholz et al. |

FOREIGN PATENT DOCUMENTS

| | | |
|---|---|---|
| DE | 697 28 268 T2 | 1/2005 |
| EP | 0 108 171 B1 | 5/1984 |
| EP | 0 306 690 B1 | 3/1989 |
| EP | 0 910 310 B1 | 4/1999 |
| EP | 0 956 189 B1 | 11/1999 |
| WO | 92/03107 A1 | 3/1992 |
| WO | 97/43983 A1 | 11/1997 |
| WO | 99/40875 A | 8/1999 |
| WO | 99/40875 A1 | 8/1999 |
| WO | 02/30322 A2 | 4/2002 |
| WO | 02/35989 A2 | 5/2002 |

OTHER PUBLICATIONS

Gefäβprothesen, BARD Peripheral Vascular.
Distaflo™ ePTFE Gefäβprothesen, BARD Peripheral Vascular.
Venaflo™ ePTFE Gefäβprothesen BARD Peripheral Vascular.

* cited by examiner

*Primary Examiner* — Bruce E Snow
*Assistant Examiner* — Brian Dukert
(74) *Attorney, Agent, or Firm* — DLA Piper LLP (US)

(57) ABSTRACT

A woven textile vascular prosthesis including a tubular trunk and at least one fork, each fork having an apex located between outgoing tubular branches with a small diameter, wherein at least a portion of a wall of the prosthesis in a zone of the apex is woven more densely than in other zones having an original weave construction.

19 Claims, 3 Drawing Sheets

WOVEN TEXTILE VASCULAR PROSTHESIS

RELATED APPLICATION

This application claims priority of German Patent Application No. 102007063265.9, filed Dec. 17, 2007, herein incorporated by reference.

TECHNICAL FIELD

This disclosure relates to a woven textile vascular prosthesis having a tubular-shaped trunk and at least one fork, each with an apex located between outgoing tubular branches having a smaller diameter.

BACKGROUND

Woven tubular vascular prostheses having a fork are known from EP 0 108 171 B1 and EP 0 910 310 B1 (which corresponds to DE 697 28 268 T2). Such forks are also referred to as furcations or bifurcations or trifurcations. The problem with vascular prostheses having forks is that leakage may occur in the furcation region, or in the crotch of the fork. This leakage is due to an additional area in the crotch region at the transition point from the large diameter to the small diameters, which cannot be covered to the required density with the number of yarns given. This problem is described in detail in DE 697 28 268 T2.

SUMMARY

We provide a woven textile vascular prosthesis including a tubular trunk and at least one fork, each fork having an apex located between outgoing tubular branches with a small diameter, wherein at least a portion of a wall of the prosthesis in a zone of the apex is woven more densely than in other zones having an original weave construction.

BRIEF DESCRIPTION OF THE DRAWINGS

Further characteristics of the disclosure can be found in the following description of representative examples and the drawings. In this case, the various characteristics can be realized individually or as a whole in combination with each other.

The drawings show.

DETAILED DESCRIPTION

Figure 1:
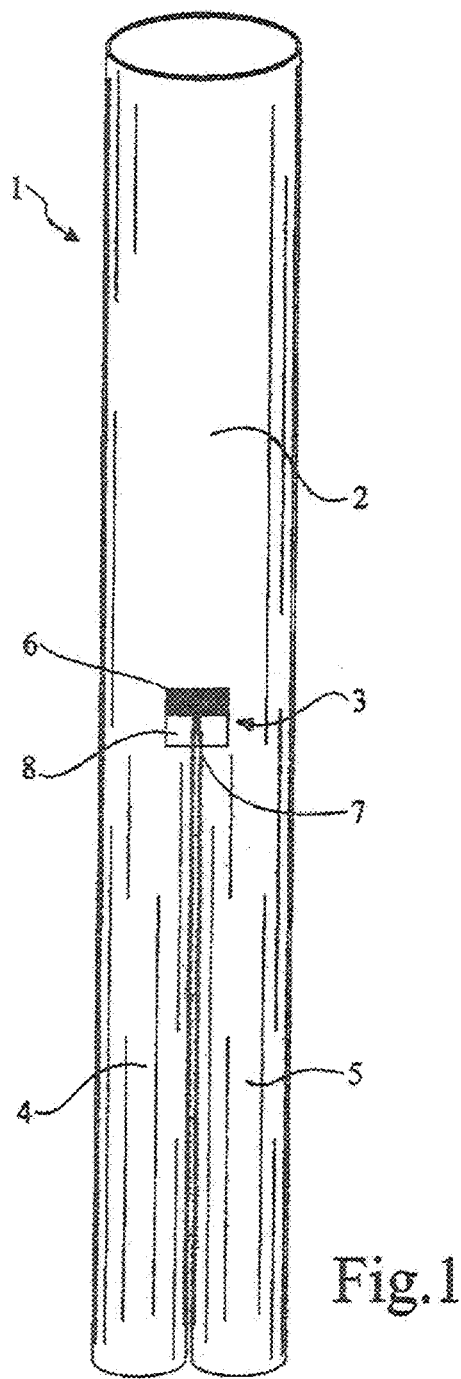
FIG. 1: a vascular prosthesis.

There should be a gradual change in the number of warp yarns to provide the regained density. In particular, sections of warp yarns that are intended for one fork should be combined with weft yarns of the other fork in the transition zone and vice versa, so that a gradual transition occurs from the trunk to the forks. Furthermore, the number of warp yarns should be increased at the transition point from the trunk to the forks.

This is achieved in our prosthesis by the wall of the prosthesis being woven more densely in the region of the apex than the original construction in the other zones. The prosthesis wall is preferably woven more densely in the region of the apex only. Preferably, the number of warp yarns does not change, nor do the weft yarns of the outgoing branches intersect.

Woven prostheses are usually denser than knitted prostheses, or they can be set to have a denser construction. If a constant number of warp yarns is processed during weaving, as is preferably the case with our prosthesis, this leads to undesirable leakage in the so-called crotch zone of the fork as a result of the additional area. This is overcome by weaving the fabric more densely in this zone than in the other zones. It is thus not necessary to interrupt the weaving process or to carry out a subsequent process. The fork arrangement is such that the warp yarns continue running from the thicker trunk into the forked branches. This is usually a bifurcation. A trifurcation or a higher number of furcations may also be provided for. The prosthesis can be manufactured by a simple process.

The splitting-up of the weft yarns at the transition point between the trunk and the branches is preferably done from one weft yarn to another. The vascular prosthesis may be pleated or unpleated. It may also be treated with conventional impregnating agents or coatings.

According to a preferred form, the denser zone is at least partly woven in a denser construction than the original construction. On the other hand, weaving the entire vascular prosthesis in this type of denser construction would be less favorable because the area per number of warp yarns would be higher in the region of the bend than in the other zones. Furthermore, floats and/or velour elements in the other zones are desirable so that the connective tissue can grow in successfully.

Another or additional way of making the region around the bend denser is for the weft yarns to be arranged closer to each other, especially packed more densely, in this zone of the construction than in the other zones. Each of these measures is enough in itself to achieve the desired density. However, combining both of these measures is particularly advantageous. The number of warp yarns is preferably constant. In particular, no new warp yarns are incorporated over the length of the prosthesis and none are removed.

According to another form, the more densely woven zone extends over at least 30 warp yarns, preferably over 30 to 130 warp yarns, depending on the diameter of the prosthesis. It is especially advantageous for the dense zone to extend over at least one repeat of the original construction in the other zones. For example, if the repeat extends over 32 warp yarns, the dense zone will preferably comprise 32, 64, 96 or 128 warp yarns.

Similarly, the more densely woven zone preferably extends over at least 10 weft yarns, especially over 10 to 50 weft yarns, preferably over 10 to 15 weft yarns. If the weft-yarn repeat comprises 16 yarns, for example, then the zone preferably extends over 16, 32 or 48 weft yarns. Particularly good results are obtained if the more densely woven zone extends over more than half of the warp yarns in the prosthesis.

The original construction of the vascular prosthesis is usually constructed so that the connective tissue can grow in easily. Therefore, certain loosening elements, such as velour loops, textured elements and floats are preferred, at least on the outer side of the vascular prosthesis. Therefore, woven constructions that allow for such variations are used as the woven constructions in the other zones. For example, suitable constructions are woven fabrics having velour elements, which are characterized, in particular, by the inner side of the woven prosthesis being untextured, while floating textured warp yarns on the outer side promote the ingrowth of connective tissue. Warp-sided twill and atlas weaves can also achieve similar effects.

In a preferred form, constructions are used in the more densely woven zone, which have no floats at all or just a few floats, and in which textured yarns, which are usually less dense than untextured yarns, are only present over short lengths. A plain weave is the most suitable dense construction. A plain weave of 1 over 1, 1 under 1 is the densest woven construction. Other constructions that are suitable for the more densely woven zone are, for example, various modified versions of the plain weave, such as panama and rib constructions, as well as small-repeat twill (e.g., T 2/1 or T 1/2 in the S or Z degree).

If the weft yarns are also compacted, so that the weft yarns lie closer together, preferably in an amount of 5 to 20%, i.e., so that they correspondingly extend over a shorter warp length, the required density can be achieved without any problems. In particular, mechanical compaction can be achieved by beating-up the weft yarns more robustly. The percentage of maximum densification or compaction will depend on the density of the weave in the original construction and on the density or the diameter of the weft yarns. Furthermore, the density of the woven fabric can be increased as a result of subsequent shrinkage by using shrink yarns in the more densely woven zone. During shrinkage, the thickness of the shrink yarns increases, whereby compaction is achieved. To prevent the formation of undulations as a result of the weft yarns shrinking, the warp yarns in the denser zone can be splayed out in a body during weaving, e.g., by using a V-rail, whereby shrinkage reduces the length of the yarns. Preferably none at all or just a few shrinkable weft yarns are used outside the denser zone.

The yarns used for the vascular prosthesis are preferably multifilament yarns. Both untextured as well as textured yarns may be used. The woven construction of the vascular prosthesis preferably comprises warp yarns made from untextured and textured yarns. In a particularly preferred form, untextured and textured yarns alternate with each other in the warp, preferably in a ratio of 1:1. The weft yarns are preferably exclusively untextured yarns. Thus, the untextured yarns predominate. However, by using a suitable construction, it is possible for the textured yarns to lie preferably on the outer surface of the prosthesis, which is beneficial to tissue ingrowth.

We therefore do not provide for subsequent sewing in the region of the apex nor for the use of additional warp yarns during the weaving process. Nevertheless, the required density in the crotch of the fork can be achieved.

The structure shown in FIG. 1 is a woven vascular prosthesis 1 having a bifurcation. The vascular prosthesis 1 has a tubular trunk 2 having a fork or bifurcation 3 and, at the branching point, gives way to two further branches or forks 4 and 5 as extensions to the trunk. The diameters of the branches, which are also tubular in shape, correspond roughly to half the diameter of the trunk.

The woven fabric of the vascular prosthesis has warp yarns running in the lengthwise direction and weft yarns circulating transversely to these. The warp yarns extend over the entire length of the vascular prosthesis and split into two halves in the bifurcation. Instead of one circulating weft yarn in the trunk, a separate weft yarn is provided for each branch from the bifurcation. In principle, the vascular prosthesis is produced in a known manner as is also described in DE 697 28 268 T2. A double flat woven fabric is produced first of all, whereby a lower layer and an upper layer are joined together at the selvedges during weaving. The prosthesis may be pleated in a known manner. If required, it may be treated with an impregnating agent made from a resorbable material. The vascular prosthesis may be manufactured as a so-called continuous woven fabric, in which a trunk 2 divides into two branches 4 and 5, which then come together again to form a new trunk after a specific distance, which subsequently divides into two forks again after a specific length. A prosthesis having a bifurcation may be obtained by cutting out suitable lengths as appropriate.

A zone 6 is located in the region of the bifurcation in trunk 2, just before the point at which it divides into the two branches 4 and 5, in which the woven fabric is denser than in the other zones. This makes the woven fabric denser in the crotch 7 of the bifurcation, which prevents the porosity from being higher here than would normally be the case. A boundary zone 8, which encompasses the denser zone 7, is shown in FIGS. 2 and 3 and is described in more detail there.

Figure 2:
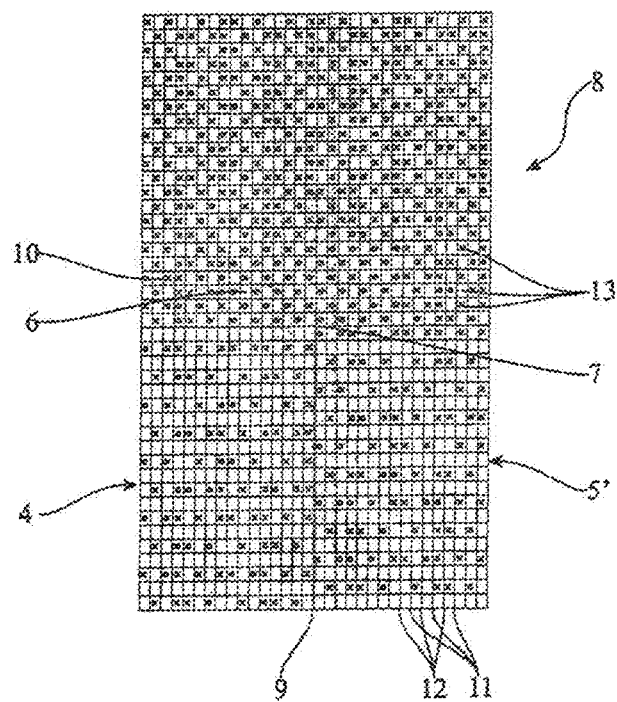
FIG. 2: a weaving pattern for one form of the prosthesis, reduced by the binding warp and weft yarns on the rear side of the prosthesis (rear wall of the tube)

FIG. 2 shows a weaving pattern for the woven fabric construction in zone 8 of FIG. 1 for one structure. The lower half has two tubular sections 4' and 5', which are separate from each other, as indicated by the separating line 9. Sections 4' and 5' are already parts of branches 4 and 5. The two tubular sections 4' and 5' join in the central zone and run into a tubular section 2', correspondingly having twice the diameter, which is part of trunk 2. The bifurcation point 7 is located at the transition point.

Figure 3:
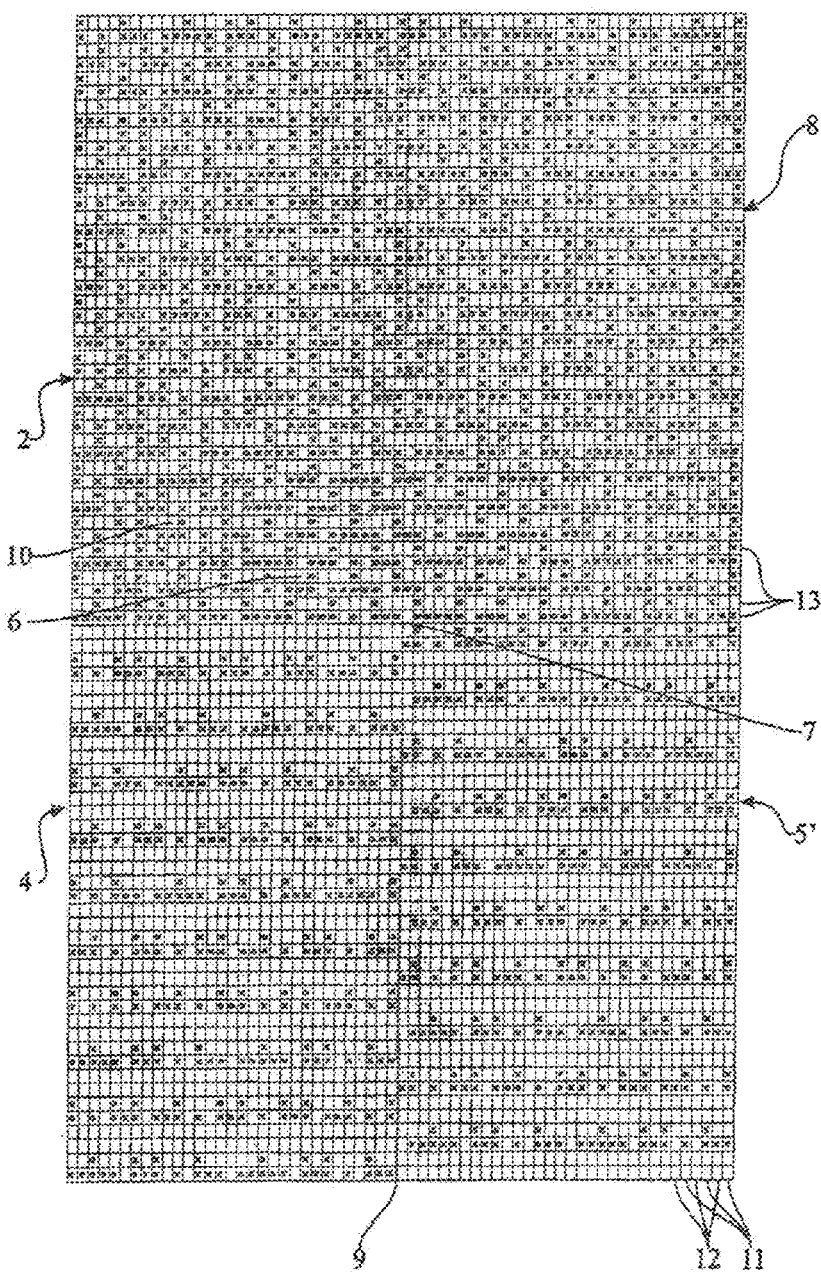
FIG. 3: a weaving pattern for the form according to FIG. 2, including the binding warp and weft yarns on the rear side of the prosthesis.

The original construction of the woven fabric as shown in FIGS. 2 and 3 is a plain weave with the addition of velour yarns, wherein the velour yarns lie on the outer side. It is already relatively dense as it is. It extends from the tubular section 2 having a large diameter and over tubes 4 and 5 having a smaller diameter, as well as to the outer edges 10 of the transition zone in the bifurcation. The construction in the more densely woven zone 6 at the transition point is a true plain weave of 1 over 1, 1 under 1 (1/1). This particularly dense weave enables the desired sealing characteristics to be achieved at the bifurcation point 7 shown in FIG. 1.

Untextured multifilament yarns 11, which alternate with textured yarns 12, are used as the warp yarns. Only untextured multifilament yarns are used as the weft yarns 13. Suitable untextured yarns are characterized as 100f 80Z 240. Suitable textured yarns are characterized as 100f 80Z 140.

FIG. 3 shows the same structure as FIG. 2, wherein, however, the rear wall of the tube is also incorporated into the weaving pattern. The weaving pattern is thus opened out in length and width.

In the more densely woven zone 6, the weft yarns may be additionally compacted in the direction of the warp yarns, whereby the density is further increased. Alternatively or additionally, shrink yarns may be used as the weft yarns in this zone.

The invention claimed is:

1. A woven textile vascular prosthesis comprising a tubular trunk and one fork, the fork having an apex located between outgoing tubular branches with a small diameter, wherein at least a portion of a wall of the prosthesis in a zone of the apex is woven more densely than in other zones of the prosthesis having an original weave construction, and wherein a more densely woven zone has a construction type that is denser than an original weave construction.

2. The woven textile vascular prosthesis according to claim 1, wherein separate weft yarns are located in the branches beginning in the apex.

3. The woven textile vascular prosthesis according to claim 1, wherein weft yarns lie closer to each other in the more densely woven zone than in the other zones.

4. The woven textile vascular prosthesis according to claim 1, wherein the denser zone extends over at least 30 warp yarns.

5. The woven textile vascular prosthesis according to claim 1, wherein the more densely woven zone extends over at least 10 weft yarns.

6. The woven textile vascular prosthesis according to claim 1, wherein the denser zone extends over at least one repeat of the original weave construction.

7. The woven textile vascular prosthesis according to claim 1, wherein the more densely woven zone extends over more than half of the warp yarns in the prosthesis.

8. The woven textile vascular prosthesis according to claim 1, wherein the original weave construction is a plain weave modified with velour yarns.

9. The woven textile vascular prosthesis according to claim 1, wherein the construction in the denser zone is a plain weave.

10. The woven textile vascular prosthesis according to claim 1, wherein the construction in the denser zone is a variation of a plain weave.

11. The woven textile vascular prosthesis according to claim 1, wherein yarns forming the prothesis are multifilament yarns.

12. The woven textile vascular prosthesis according to claim 1, comprising a warp comprising untextured and textured yarns.

13. The woven textile vascular prosthesis according to claim 1, comprising untextured and textured yarns alternating in a warp.

14. The woven textile vascular prosthesis according to claim 1, comprising weft yarns of exclusively untextured yarns.

15. The woven textile vascular prosthesis according to claim 1, comprising weft yarns, at least outside the more densely woven zone, which are shrink yarns that have shrunk.

16. The woven textile vascular prosthesis according to claim 1, wherein the more densely woven zone is free of additional warp yarns.

17. The woven textile vascular prosthesis according to claim 1, wherein the number of warp yarns is constant over the entire length of the prosthesis.

18. The woven textile vascular prosthesis according to claim 1, wherein the densely woven zone extends over 30 to 130 warp yarns.

19. The woven textile vascular prosthesis according to claim 1, wherein the more densely woven zone extends over 10 to 15 weft yarns.

* * * * *